United States Patent [19]
Baumann et al.

[11] 3,971,821
[45] July 27, 1976

[54] PRODUCTION OF AMINOBENZALDEHYDES

[75] Inventors: Hans Baumann, Ludwigshafen; Klaus Grychtol, Bad Durkheim; Andreas Oberlinner, Ludwigshafen, all of Germany

[73] Assignee: BASF Aktiengesellschaft, Ludwigshafen (Rhine), Germany

[22] Filed: Dec. 9, 1974

[21] Appl. No.: 531,090

[30] Foreign Application Priority Data
Dec. 20, 1973 Germany............................ 2363458

[52] U.S. Cl. ......................... 260/465 E; 260/471 R; 260/566 A; 260/566 B; 260/566 F; 260/577
[51] Int. Cl.² .............. C07C 87/60; C07C 101/00; C07C 121/78
[58] Field of Search ............. 260/465 E, 577, 471 R

[56] References Cited
OTHER PUBLICATIONS

Olah: Friedel–Crafts and Related Reactions, Interscience Publishers, N.Y., vol. III, Part 2, pp. 1211–1212, 1214, 1219–1223, 1230–1231, (1964).

*Primary Examiner*—Lewis Gotts
*Assistant Examiner*—Dolph H. Torrence
*Attorney, Agent, or Firm*—Johnston, Keil, Thompson & Shurtleff

[57] ABSTRACT

Aminobenzaldehyde compounds and a process for their production by the reaction of an aniline with a formamide in the presence of an acid halide with or without a following reaction with a nitrogen compound. The products are starting materials for the production of optical brighteners, dyes, plant protection agents and medicaments.

7 Claims, No Drawings

PRODUCTION OF AMINOBENZALDEHYDES

The invention relates to aminobenzaldehyde compounds and a process for their production by the reaction of an aniline with a formamide in the presence of an acid halide followed if desired by reaction with a nitrogen compound.

It is known from Houben-Weyl, "Methoden der organischen Chemie", volume 7/1, pages 29 to 32, that alkylanilines can be reacted with a formylating agent and phosphorus oxychloride to form p-aminobenzaldehydes. Reference is made to the fact that only certain aromatics, for example those which are more readily substituted than benzene, can be reacted in this way. Reactions of alkylanilines bearing electronegative radicals as substituents in the o-position or the m-position to the alkylamino group are not described. It must be assumed that such substances, for example o-nitro-N-alkylanilines or m-nitro-N-alkylanilines also cannot be reacted because Houben-Weyl expressly states on page 31 which groups of substances (namely for example phenols and phenol ethers) can bear two substituents in the o-position or the m-position to one another and can be subjected to the Vilsmeier reaction. The same teaching is given by Organikum (VEB Deutscher Verlag der Wissenschaften, Berlin 1968), pages 310 to 312. It is understandable that a Vilsmeier reaction would not be successful in the case of electronegative substituents on the benzene nuclei of anilines because according to G. Olah, "Friedel-Crafts and Related Reactions" (Interscience Publishers, N.Y. 1964) volume III, part 2, page 1214, the presence of a strongly reactive (labile) hydrogen atom on the aromatic nucleus is necessary for the successful use of the Vilsmeier reaction. Electronegative substituents such as nitro, cyano or carboxylic ester groups deactivate the aromatic nucleus and prevent the formation of labile hydrogen atoms. This is shown for example by an article in Chem. Ber., volume 92 (1959), pages 141 to 144, because a Vilsmeier formylation of 1-nitroazulene is not successful whereas it proceeds easily and under mild conditions with unsubstituted azulene. The publication expressly teaches that a nitro group stabilizes the azulene as an electron-attracting substituent, decreases the electron density in the ring and thus decreases the formation of labile hydrogen atoms.

One object of this invention are new aminobenzaldehyde compounds.

Another object of this invention is a new process of producing the new aminobenzaldehyde compounds in a good yield and high purity in a simple way.

We have found that an aminobenzaldehyde compound of the formula:

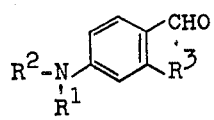

(Ia)

in which $R^1$ and $R^2$ may be identical or different and each is an aliphatic or araliphatic radical and $R^3$ is nitro, cyano, or the radical

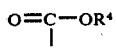

in which $R^4$ is an aliphatic, cycloaliphatic, araliphatic or aromatic radical is advantageously obtained by the reaction of an aromatic compound with a formamide and an acid halide by reacting an aniline of the formula (II):

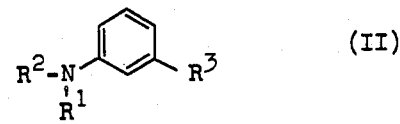

(II)

in which $R^1$, $R^2$ and $R^3$ have the above meanings in the presence of an acid halide of phosphorous acid, phosphoric acid, carbon dioxide, oxalic acid, sulfurous acid or sulfuric acid with a formamide of the formula (III):

(III)

in which $R^5$ and $R^6$ may be identical or different and each is hydrogen or an aliphatic or aromatic radical, or $R^5$ and $R^6$ together with adjacent nitrogen atom are members of a heterocyclic ring.

We have further found that the end product (Ia) thus obtained may be advantageously reacted with a nitrogen compound of the formula (IV):

$$R^7-NH_2 \qquad (IV)$$

in which $R^7$ is an aliphatic, araliphatic, cycloaliphatic or aromatic radical or the radical —OH or the radical

or the radical —NH—$R^4$ wherein $R^4$ has the above meanings to form an aminobenzaldehyde compound of the formula (Ib):

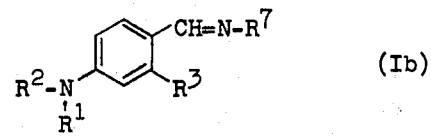

(Ib)

in which $R^1$, $R^2$, $R^3$ and $R^7$ have the above meanings.

When m-nitrodimethylaniline and dimethylformamide are used the reaction may be represented by the following equation:

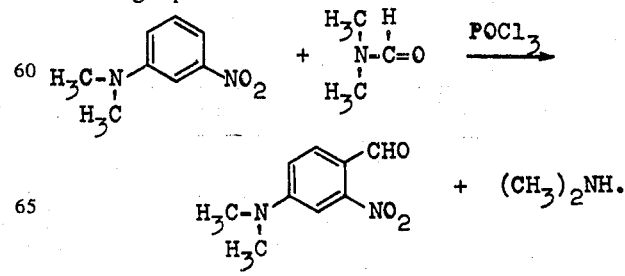

Having regard to the prior art the process according to the invention gives the new aminobenzaldehyde compounds simply in good yields and purity. It is possible by the new process to prepare substances not hitherto described by a process which is economical and at the same time is suitable on an industrial scale. Amines with electronegative substiuents are thus obtained in high yields. All these advantageous results of the process are surprising having regard to the prior art.

Preferred starting materials (II), (III) and (IV) and therefore preferred end products (Ia) and (Ib) and thus end products (I) having the formula:

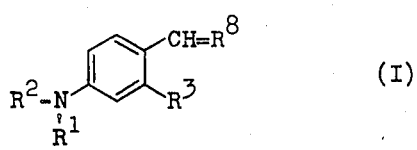
(I)

in which $R^1$ and $R^2$ are identical or different and each is an aliphatic or araliphatic radical and $R^3$ is nitro, cyano or the radical

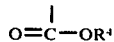

in which $R^4$ is an aliphatic, cycloaliphatic, araliphatic or aromatic radical, and $R^8$ is oxygen or the radical $=N-R^7$, $R^7$ is an aliphatic, araliphatic, cycloaliphatic or aromatic radical or the radical —OH or the radical

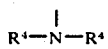

or the radical —NH—$R^4$ in which $R^4$ has the above meanings, are those in whose formulae $R^1$ and $R^2$ are identical or different and each is alkyl of one to eight and particularly one to four carbon atoms, or aralkyl of seven to twelve carbon atoms, $R^3$ is nitro, cyano or the radical

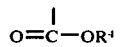

in which $R^4$ is alkyl of one to eight and preferably one to four carbon atoms, cyclopentyl, aralkyl of seven to twelve carbon atoms, phenyl, $R^5$ and $R^6$ may be identical or different and each is alkyl of one to four carbon atoms, phenyl, or hydrogen, $R^5$ and $R^6$ may moreover together with the adjacent nitrogen atom be members of a five-membered or six-membered heterocyclic ring which may contain an oxygen atom as well as the nitrogen atom, $R^7$ is alkyl of one to eight and preferably one to four carbon atoms, cyclopentyl, cyclohexyl, aralkyl of seven to twelve carbon atoms, phenyl or —OH or

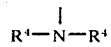

or —NH—$R^4$ in which $R^4$ has the above meanings, $R^8$ is oxygen or $=N-R^7$ in which $R^7$ has the above preferred meaning. The said radicals and rings may bear (as substituents) groups and/or atoms which are inert under the reaction conditions, for example bromine, iodine and particularly chlorine, alkoxy of one to four carbon atoms, hydroxy, cyano, carbalkoxy of two to four carbon atoms. If desired, instead of the starting materials (II) use may be made of substances which form these materials (II) under the reaction conditions, for example instead of an aminobenzonitrile such as m-dimethylaminobenzonitrile the appropriate amount of an aminobenzamide such as m-dimethylaminobenzamide, with larger amounts, for example from twice to ten times the amounts of acid halide and starting material (III) based on starting material (II).

Examples of suitable starting materials (II) are: m-nitrodimethylaniline, m-nitrodiethylaniline, m-nitrodibenzylaniline, m-nitrodichloroethylaniline, m-nitro-N-methyl-N-β-chloroethylaniline, m-nitrodimethoxyethylaniline, m-nitro-N,N-di-n-hexylaniline, m-nitrodi-n-butylaniline, m-nitro-N-methyl-N-ethylaniline, m-nitro-N-benzyl-N-methylaniline, m-nitro-N,N-di-(β-chloroethyl)-aniline, methyl m-dimethylaminobenzoate, ethyl m-diethylaminobenzoate, isopropyl m-dipropylaminobenzoate, methyl m-dibutylaminobenzoate, m-diethylaminobenzonitrile, m-dimethylaminobenzonitrile; m-aminobenzonitriles substituted on the nitrogen atom in the said manner, and the cyclohexyl, cyclopentyl, n-hexyl, n-butyl, tert.-butyl, isobutyl, benzyl, phenyl, toluyl, p-chlorophenyl and ethoxyethyl esters of m-aminobenzoic acid.

Examples of formamides which are suitable as starting materials (III) are: formamide, formanilide, N-formylpiperidine, N-formylpyrrolidine, N-formylmorpholine, N,N-diethylformamide, N-isobutylformamide, N-methylformamide, form-(p-chloro)-anilide and particularly N-methylformanilide or N,N-dimethylformamide.

The starting material (III) may if desired also be used in the form of a complex compound with a dialkyl sulfate. Dimethyl or diethyl sulfate is suitable and may be present in such complex compounds in a ratio of from 1 to 1.2 moles per mole of starting material (III).

The starting material (II) is reacted with starting material (III) in the presence of an acid halide, preferably an acid bromide and particularly an acid chloride, of phosphorus acid, phosphoric acid, carbonic acid, oxalic acid, sulfurous acid or sulfuric acid, conveniently oxalyl chloride, oxalyl bromide, thionyl chloride, phosphorus trichloride, phosphorus tribromide, sulfuryl chloride and preferably phosphorus oxychloride or phosgene. The acid halide is used in the stoichiometric amount or in excess and conveniently in an amount of from one to eight moles of acid halide per mole of starting material (II). The reaction of the starting material (III) with the starting material (II) may be carried out with a stoichiometric amount or an excess and advantageously with an amount of from one to four moles of starting material (III) per mole of starting material (II). In this process it is convenient to allow the acid halide and the starting material (III) to act on one another first so that the addition product which is known for the Vilsmeir method is prepared. The adducts may be represented as follows, for example (Houben-Weyl, loc. cit., page 30) in the case when phosphorus oxychloride is used:

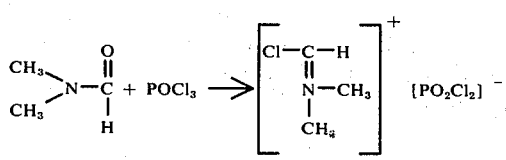

The adduct need not however have the said structure in every case and the formation of an adduct is not a prerequisite to being able to carry out the process according to the invention.

The reaction is carried out as a rule at a temperature of from −10° to +120°C and preferably at from 20° to 80°C at atmospheric or superatmospheric pressure, continuously or batchwise. It is possible, particularly in the case of gaseous acid halides, to use an organic solvent which is inert under the reaction conditions, for example a cyclic carboxamide such as N-methylpyrrolidone; a hydrocarbon such as cyclohexane, benzene or toluene; a chlorohydrocarbon such as chloroform or carbon tetrachloride; an ether such as tetrahydrofuran, dioxane or glycol dimethyl ether; or appropriate mixtures. The amount of solvent is generally from 10 to 1000% by weight based on starting material (II). A suitable starting material (III), for example formamide, is used as the reaction medium in many cases.

The reaction may be carried out as follows: a mixture of the starting materials (II) and (III) and the acid chloride is kept at the reaction temperature for from half an hour to twenty hours. The end product (Ia) is then isolated by a conventional method, for example by treating the mixture with ice-water, if desired while neutralizing the acid with an alkaline compound, filtration and washing the precipitate formed.

The end products (Ia) thus obtained may be further processed in this form but they are advantageously reacted with the nitrogen compound (IV) to form a Schiff's base, oxime or hydrazone. The substance (IV) may be used in a stoichiometric amount or in excess, preferably in an amount of from 2 to 6 and preferably from 2 to 3 moles per mole of end product (Ia). The hydroxylamine is used as a rule in the form of a salt. Examples of suitable salts are the chloride, sulfate, formate or acetate of hydroxylamine.

Examples of starting materials (IV) are: hydroxylamine, methylamine, ethylamine, isopropylamine, n-propylamine, n-butylamine, isobutylamine, tert.-butylamine, sec.-butylamine, pentylamine, cyclohexylamine, cyclopentylamine, benzylamine, β-naphthylamine, phenylethylamine, aniline, o-methylaniline, m-methylaniline, p-methylaniline, p-nitroaniline, 2,4-dinitroaniline, p-bromoaniline and o-methoxyaniline; also corresponding hydrazines unsymmetrically substituted twice or once by the abovementioned radicals $R^7$.

The reaction is generally carried out at a temperature of from −10° to 110°C and preferably from 10° to 80°C at atmospheric or superatmospheric pressure and continuously or batchwise. Solvents which are inert under reaction conditions may be used to dissolve or suspend the starting materials or the reaction mixture. Water and organic solvents having a boiling point at atmospheric pressure or at a pressure of up to 10 atmospheres of more than 100°C and preferably from 60° to 190°C at atmospheric pressure are advantageous. Examples of suitable solvents are: water; alcohols such as ethanol, n-butanol, isobutanol, tert.-butanol, cyclohexanol, propanol and particularly methanol; sulfoxides such as dimethyl sulfoxide; ethers, for example n-butyl ethyl ether, di-n-butyl ether, diisoamyl ether, diisopropyl ether, anisol, phenetol, cyclohexyl methyl ether, diethyl ether, tetrahydrofuran, thioanisol, or β,β'-dichlorodiethyl ether; inorganic or organic acids, for example acetic acid, hydrochloric acid, sulfuric acid, phosphoric acid, boric acid or chloroacetic acid; and appropriate mixtures. The solvent is conveniently used in an amount of from 5 to 1000% by weight and preferably from 5 to 50% by weight based on starting material (IV). In the case of the production of oximes the reaction can be carried out also in an alkaline medium, for example by means of caustic soda solution, sodium carbonate, sodium bicarbonate or sodium acetate.

The reaction may be carried out as follows: a mixture of the substances (Ia) and (IV) with or without a solvent is kept for from half an hour to ten hours at the reaction temperature. The end product (Ib) is then isolated by a conventional method, for example by filtration and if necessary washing the filter cake with a suitable solvent such as ethanol. Houben-Weyl, loc. cit., pages 453 to 466 may be referred to for details of the reaction conditions in the production of hydrazones, oximes and Schiff's bases.

The new compounds (I) which can be prepared according to the process of the invention are valuable starting materials for the production of optical brighteners, dyes, plant protection agents and medicaments. German Patent . . . (Patent application No. P 23 63 459.5 — O.Z. No. 30,275) is referred to for details of uses of compounds (Ia) which bear a nitro group in the 2-position.

Substances (Ia) may be converted by reaction with compounds having reactive methyl or methylene groups, as for example:

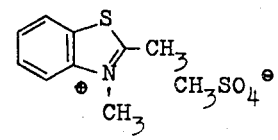

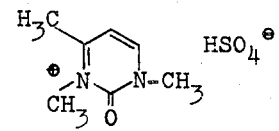

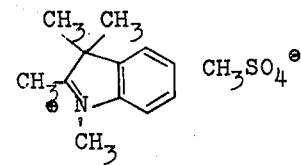

into basic dyes which give red dyeings fast to water and to washing on polyacrylonitrile cloth.

Similarly compounds (Ia) with the carboxylic ester group or cyano group in the 2-position may be condensed with compounds bearing reactive methyl or methylene groups, for example:

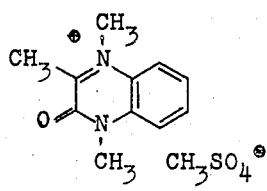 and 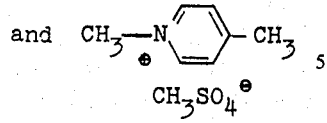

to give basic dyes and with appropriate compounds, for example:

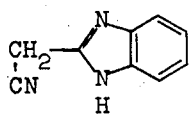

to give disperse dyes which give bright blue or orange dyeings on polyacrylonitrile cloth and bright yellow fluorescent dyeings on polyester, polyamide (Perlon) and cellulose acetate cloth.

These compounds are also valuable starting products for the synthesis of crystal violet lactone and analogous triphenylmethane compounds which may be obtained by condensation with dialkylanilines, oxidation and alkaline cyclization. For example crystal violet lactone may be obtained as follows:

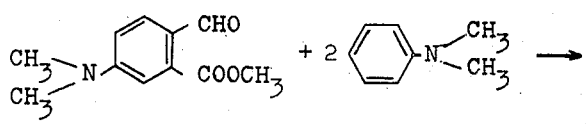

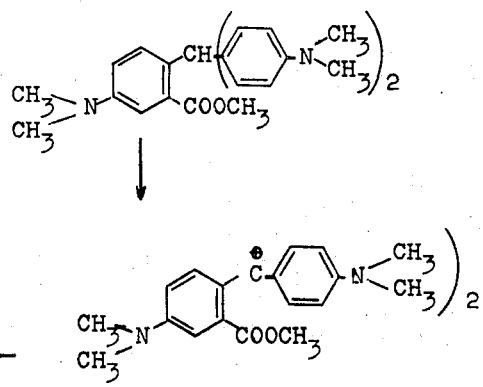

Such compounds are used in the production of carbonless reaction copying papers.

The compounds which can be prepared according to the process of the invention are aminobenzaldehyde compounds of the formula:

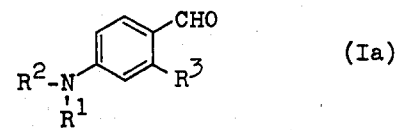 (I)

in which $R^1$ and $R^3$ may be identical or different and each is an aliphatic or araliphatic radical and $R^3$ is nitro, cyano, $$O=\overset{|}{C}-OR^4$$

in which $R^4$ is an aliphatic, cycloaliphatic, araliphatic or aromatic radical, and $R^8$ is oxygen or $=N-R^7$, $R^7$ is an aliphatic, araliphatic, cycloaliphatic or aromatic radical, —OH, $$R^4-\overset{|}{N}-R^4$$

or —NH—$R^4$ in which $R^4$ has the above meanings, aminobenzaldehyde compounds of the formula (Ia):

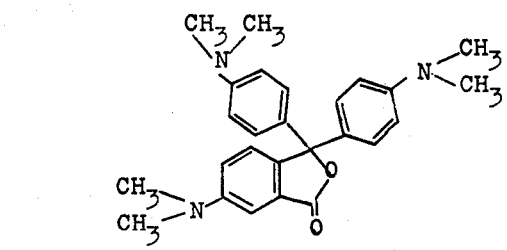 (Ia)

in which $R^1$ and $R^2$ may be identical or different and each is an aliphatic or araliphatic radical and $R^3$ is nitro, cyano or $O=\overset{|}{C}-OR^4$ in which $R^4$ is an aliphatic, cycloaliphatic, araliphatic or aromatic radical, and aminobenzaldehyde compounds of the formula (Ib):

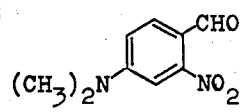 (Ib)

in which $R^1$, $R^2$, $R^3$ and $R^7$ have the above meanings. All end products (I), (Ia) and (Ib) in whose formulae the radicals $R^1$ to $R^8$ have the said preferred meanings are particularly advantageous for the said uses. The following are examples of preferred end products (I):

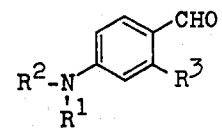

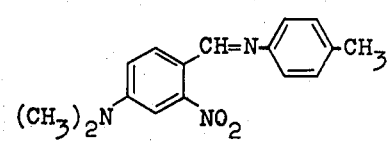

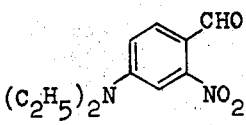

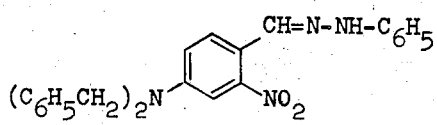

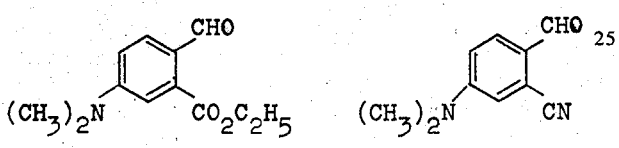

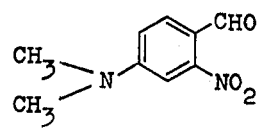

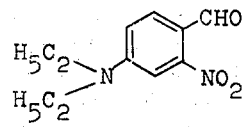

The following Examples illustrate the invention. The parts specified in the Examples are parts by weight. They bear the same relation to parts by volume as the kilogram to the liter.

EXAMPLE 1

720 parts of phosphorus oxychloride is added at 25°C to a solution of 498 parts of m-nitrodimethylaniline in 1800 parts by volume of dimethylformamide. The mixture is then heated within 1 hour to 75° to 80°C and stirred at this temperature for six hours. After the solution has cooled it is poured into 6000 parts of icewater. The precipitate is suction filtered, washed and recrystallized from acetone. 385 parts (66% of theory) of 2-nitro-4-dimethylaminobenzaldehyde having a melting point of 115° to 116°C is obtained.

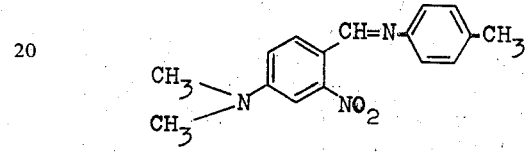

EXAMPLE 2

38 parts of m-nitrodiethylaniline is introduced into a mixture of 48 parts of phosphorus oxychloride in 120 parts of dimethylformamide. After having been stirred for six hours at 60°C the mixture is poured into icewater and the precipitate is suction filtered, washed free from acid and recrystallized from acetone. 12 parts (27% of theory) of 2-nitro-4-diethylaminobenzaldehyde having a melting point of 75° to 77°C is obtained.

EXAMPLE 3

194 parts of 2-nitro-4-dimethylaminobenzaldehyde is dissolved in 800 parts of ethanol at 80°C and after 115 parts of p-toluidine and 1 part of concentrated hydrochloric acid has been added the whole is kept for 1 hour at 80°C. The red azomethine which crystallizes out after cooling is suction filtered and dried. The yield is 255 parts (90% of theory) of 2-nitro-4-dimethylaminobenzaldehyde-p-toluidinimine having the melting point 114° to 116°C.

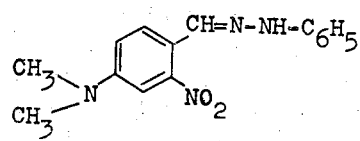

EXAMPLE 4

9.7 parts of 2-nitro-4-dimethylaminobenzaldehyde is dissolved in 50 parts of ethanol at 80°C, 6.5 parts of phenylhydrazine and 1 part by volume of hydrochloric acid are added and the mixture is kept for 1 hour at 80°C. After having been cooled the mixture is suction filtered and the end product is washed with ethanol. The yield is 11 parts (77% of theory) of 2-nitro-4-dimethylaminobenzaldehydephenylhydrazone having a melting point of 182° to 183°C:

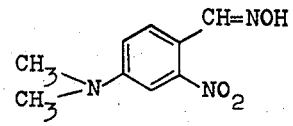

EXAMPLE 5

9.7 parts of 2-nitro-4-dimethylaminobenzaldehyde is dissolved in 50 parts of ethyl alcohol and a solution of 4.1 parts of hydroxylamine hydrochloride and 5 parts of sodium acetate in water is added. After the mixture has been boiled for one hour it is suction filtered. 7.5 parts (71% of theory) of 2-nitro-4-dimethylaminobenzaldoxime is obtained having a melting point of 140° to 143°C:

EXAMPLE 6 a. 32 parts of m-nitrobenzylaniline is introduced into a mixture of 20 parts of N-methylformanilide and 23 parts of phosphorus oxychloride and stirred for 12 hours at 70°C. The mixture is poured onto 100 parts of water and suction filtered. 20 parts (57% of theory) of 2-nitro-4-dibenzylaminobenzaldehyde having a melting point of 67° to 70°C is obtained.

b. 5 parts of the aldehyde is dissolved in 20 parts of ethyl alcohol and 6 parts of phenylhydrazine is added. The mixture is kept for 30 minutes at 80°C, suction filtered and dried. The yield is 6 parts (96% of theory) of 2-nitro-4-dibenzylaminobenzaldehydephenylhydrazone having a melting point of 198° to 199°C.

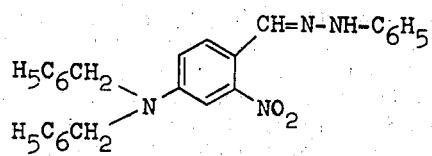

EXAMPLE 7

340 parts of phosphorus oxychloride is added at 15°C to 290 parts of dimethylformamide. 360 parts of m-dimethylaminobenzoic acid methyl ester is added at 25°C and the mixture is stirred for 6 hours. The reaction mixture is poured onto ice-water and then 25% by weight ammonia solution is added until turbidity begins to occur. The precipitate is suction filtered and washed with water. The yield is 152 parts of 2-carbomethoxy-4-dimethylaminobenzaldehyde (37% of theory) having a melting point of 79° to 80°C.

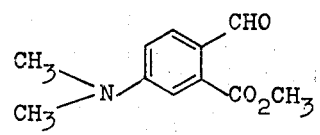

EXAMPLE 8

425 parts of phosphorus oxychloride is added at 15°C to 360 parts of dimethylformamide. 487 parts of m-dimethylaminobenzoic acid ethyl ester is added at 25°C. The mixture is stirred for another three hours and the procedure of Example 7 is followed. The yield is 209 parts (38% of theory) of 2-carboethoxy-4-dimethylaminobenzaldehyde having a melting point of 63° to 65°C.

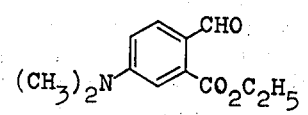

EXAMPLE 9

34 parts of phosphorus oxychloride is added at 25°C to 29 parts of dimethylformamide. 41 parts of propyl m-dimethylaminobenzoate is added at the same temperature, the mixture is stirred for another 3 hours and a procedure analogous to Example 7 is followed. The yield is 16 parts (33% of theory) of 2-carbopropoxy-4-dimethylaminobenzaldehyde of the melting point 48° to 50°C:

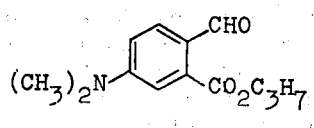

EXAMPLE 10

34 parts of phosphorus oxychloride is added at 25°C to 29 parts of dimethylformamide. 41 parts of isopropyl m-dimethylaminobenzoate is added at the same temperature, the mixture is stirred for another three hours and a procedure analogous to that described in Example 7 is followed. The yield is 11 parts (24% of theory) of 2-carboisopropoxy-4-dimethylaminobenzaldehyde having a melting point of 35° to 37°C:

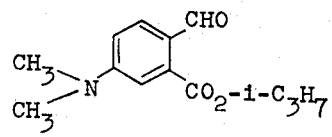

EXAMPLE 11 a. 34 parts of phosphorus oxychloride is added at 25°C to 29 parts of dimethylformamide. 29 parts of m-dimethylaminobenzonitrile is added, the mixture is stirred for another three hours and the reaction is continued in analogy to Example 7. The yield is 6 parts (17% of theory) of 2-cyano-4-dimethylaminobenzaldehyde having a melting point of 110° to 112°C.

b. The same end product is obtained in the same yield and purity when the m-dimethylaminobenzonitrile is replaced by 33 parts of m-dimethylaminobenzamide and 68 parts of phosphorus oxychloride and 50 parts of dimethylformamide are used:

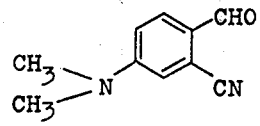

EXAMPLE 12

21 parts of 2-carbomethoxy-4-dimethylaminobenzaldehyde is dissolved in 70 parts by volume of ethanol, 10.8 parts of phenylhydrazine is added and the whole is heated at 80°C under reflux for 3 hours. After the mixture has been cooled it is suction filtered. The yield is 25 parts of 2-carbomethoxy-4-dimethylbenzaldehyde phenylhydrazone having a melting point of 105° to 106°C:

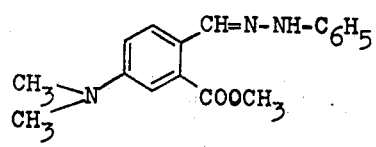

EXAMPLE 13

61.5 parts (65% of theory) of 2-nitro-4-diethylaminobenzaldehyde-p-toluidinimine having a melting point of 65° to 66°C:

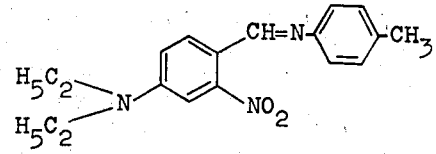

is obtained from 67 parts of 2-nitro-4-diethylaminobenzaldehyde analogously to Example 3.

We claim:

1. A process for the production of an aminobenzaldehyde compound of the formula

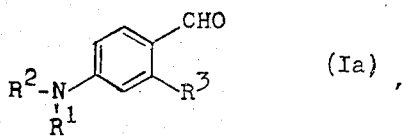

wherein $R^1$ and $R^2$ may be identical or different and each is alkyl of 1 to 8 carbon atoms or aralkyl of 7 to 12 carbon atoms; and $R^3$ is nitro, cyano or

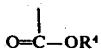

in which $R^4$ is alkyl of 1 to 8 carbon atoms, cyclopentyl, aralkyl of 7 to 12 carbon atoms or phenyl; which process comprises reacting an aniline of the formula

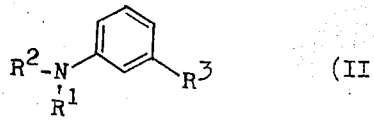

wherein $R^1$, $R^2$ and $R^3$ have the above-noted meanings, in the presence of an acid halide of phosphorous acid, phosphoric acid, carbonic acid, oxalic acid, sulfurous acid or sulfuric acid with a formamide of the formula

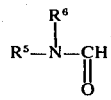

wherein $R^5$ and $R^6$ may be identical or different and each is hydrogen, alkyl of 1 to 4 carbon atoms or phenyl, or $R^5$ and $R^6$ together with the adjacent nitrogen atom may further form a heterocyclic ring member selected from the group consisting of piperidine, pyrrolidine and morpholine, with the proviso that said $R^1$ to $R^6$ may further contain substituents which are inert under the reaction conditions.

2. A process as claimed in claim 1 wherein the reaction is carried out with from 1 mole to 4 moles of starting material (III) per mole of starting material (II).

3. A process as claimed in claim 1 wherein the reaction is carried out with from 1 mole to 8 moles of acid halide per mole of starting material (II).

4. A process as claimed in claim 1 wherein the reaction is carried out with oxalyl chloride, oxalyl bromide, thionyl chloride, phosphorus trichloride, phosphorus tribromide, sulfuryl chloride, phosphorus oxychloride or phosgene.

5. A process as claimed in claim 1 wherein the reaction is carried out at a temperature of from −10° to +120°C.

6. A process as claimed in claim 1 wherein the reaction is carried out at a temperature of from +20° to +80°C.

7. A process as claimed in claim 1 wherein the reaction is carried out in the presence of an organic solvent which is inert under the reaction conditions in an amount of from 10 to 1000% by weight based on starting material (II).

* * * * *